United States Patent [19]
Morita

[11] Patent Number: 6,042,595
[45] Date of Patent: Mar. 28, 2000

[54] LANCET APPARATUS FOR PRODUCING A PRECISELY CONTROLLED INCISION

[75] Inventor: Susumu Morita, Nishinomiya, Japan

[73] Assignee: Apls Co., Ltd., Okuyama-ken, Japan

[21] Appl. No.: 09/290,598

[22] Filed: Apr. 13, 1999

[30] Foreign Application Priority Data

Mar. 2, 1999 [JP] Japan .................................. 11-054038

[51] Int. Cl.$^7$ ................................................. A61B 17/14
[52] U.S. Cl. .......................................................... 606/181
[58] Field of Search .................................... 606/181, 182, 606/180, 183, 184, 185; 128/770, 771

[56] References Cited

U.S. PATENT DOCUMENTS

| | | |
|---|---|---|
| 4,064,871 | 12/1977 | Reno . |
| 4,157,086 | 6/1979 | Maiorano et al. . |
| 4,539,988 | 9/1985 | Shirley et al. . |
| 4,628,929 | 12/1986 | Intengan et al. . |
| 4,643,189 | 2/1987 | Mintz . |
| 5,133,730 | 7/1992 | Biro et al. . |
| 5,476,474 | 12/1995 | Davis et al. ............................. 606/182 |
| 5,755,733 | 5/1998 | Morita . |
| 5,782,852 | 7/1998 | Foggia et al. . |
| 5,797,940 | 8/1998 | Mawhirt et al. . |
| 5,851,215 | 12/1998 | Mawhirt et al. ......................... 606/181 |

Primary Examiner—Michael Buiz
Assistant Examiner—Kevin Truong
Attorney, Agent, or Firm—Leydig, Voit & Mayer, Ltd.

[57] ABSTRACT

An apparatus for producing a precisely controlled incision in a bodily surface is provided. The incision device includes a housing and a lancet blade carried by a lancet guide assembly. The lancet guide assembly includes a lancet guide arm mounted within the housing for pivotal movement and a guide surface. The guide surface guides the lancet blade through an arcuate cutting stroke during which the lancet blade extends through an opening in the housing as the lancet guide arm is pivoted between an unfired and a fired position The incision device also includes a trigger mechanism having a trigger arm mounted in the housing for pivotal movement between a ready-to-fire position and firing position. A spring element is arranged within the housing such that it is an unbiased condition when the trigger arm is in the ready-to-fire position and is biased as the trigger arm pivots towards the firing position. The trigger mechanism and spring element are configured such that the biased spring element is released when the trigger arm reaches the firing position and the spring is arranged such that when it is released it exerts a force on the lancet guide arm which pivots the guide arm from the unfired to the fired position and thereby moves the lancet blade through the cutting stroke.

20 Claims, 12 Drawing Sheets

LANCET APPARATUS FOR PRODUCING A PRECISELY CONTROLLED INCISION

FIELD OF THE INVENTION

This invention generally relates to a lancet apparatus for producing a precisely controlled incision in the skin or other bodily surface of a patient, for example in a heel, and, more particularly, to disposable incision lancet apparatus which can be manufactured economically and has a very stable construction.

BACKGROUND OF THE INVENTION

Various different types of devices are commercially available which can be used to puncture or pierce a patient's skin. These include devices, such as those disclosed in U.S. Pat. Nos. 5,133,730 and 5,755,733, which are designed to prick the patient skin, for example a finger tip, as well as devices that are configured to produce an incision of a uniform length and depth in the skin.

As will be appreciated, devices which can produce a precisely controlled uniform incision can be used in conjunction with a variety of different medical tests or procedures including, for example, bleed time tests and for drawing blood for subsequent collection. More particularly, one important use for such incision devices is to produce an incision in the skin of an infant, generally in the heel, so as to enable blood to be collected for tests, such as metabolic screening tests.

Available incision devices generally utilize a spring arrangement to produce the energy necessary to drive the cutting blade through the patient's skin. With these devices, such as for example the device disclosed in U.S. Pat. No. 4,643,189, a spring is typically assembled into the device in a biased condition so that it is storing the energy which will be used to drive the cutting blade when the device is triggered. The biased spring, however, adversely effects the stability of the device. In particular, the biased spring can make accidental or premature triggering or discharge of the device, which can occur simply through inadvertent touching of the trigger, much more likely. Moreover, having the spring in a biased condition also places many of the other components of the device under stress resulting in an overall reduction in the shelf-life of the device.

Since it is generally preferable to design these devices so that they are disposable after a single use, minimizing material, manufacturing and assembly costs is always an important consideration for producing a commercially viable product. However, assembling the spring in a biased condition makes the device more difficult to manufacture, sometimes requiring the provision of special jigs, resulting in increased manufacturing and assembly costs for the device. Additionally, if provisions, such as safety caps, are included to help prevent premature firing or discharge of the device, it can further increase the material, manufacturing and assembly costs.

OBJECTS AND SUMMARY OF THE INVENTION

In view of the foregoing, it is a general object of the present invention to overcome the problems associated with the manufacture and use of known disposable skin incision devices.

A more specific object of the present invention is to provide an apparatus for producing a uniform skin incision which can be manufactured and assembled in a cost-efficient manner.

Another object of the invention is to provide an incision apparatus which has a stable construction which helps prevent accidental discharge of the incising element and enables the apparatus to have a long shelf-life.

A further object of the present invention is to provide an incision apparatus which can be sterilized and packaged in a cost-efficient manner.

The present invention provides these and other advantages and overcomes the drawbacks of the prior art by providing an incision apparatus which has a relatively simple and stable construction which makes it very difficult to trigger the device inadvertently and also enables the device to manufactured and assembled in a cost effective manner. The incision device includes a housing and a lancet blade carried by a lancet guide assembly. The lancet guide assembly includes a lancet guide arm mounted within the housing for pivotal movement and a guide surface. The guide surface guides the lancet blade through an arcuate cutting stroke during which the lancet blade extends through an opening in the housing as the lancet guide arm is pivoted between an unfired and a fired position.

The incision device also includes a trigger mechanism having a trigger arm mounted in the housing for pivotal movement between a ready-to-fire position and firing position. A spring element is arranged within the housing such that it is an unbiased condition when the trigger arm is in the ready-to-fire position and is biased as the trigger arm pivots towards the firing position. The trigger mechanism and spring element are configured such that the biased spring element is released when the trigger arm reaches the firing position and the spring is arranged such that when it is released it exerts a force on the lancet guide arm which pivots the guide arm from the unfired to the fired position and thereby moves the lancet blade through the cutting stroke.

These and other features and advantages of the invention will be more readily apparent upon reading the following description of a preferred exemplary embodiment of the invention and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENT

Figure 1:
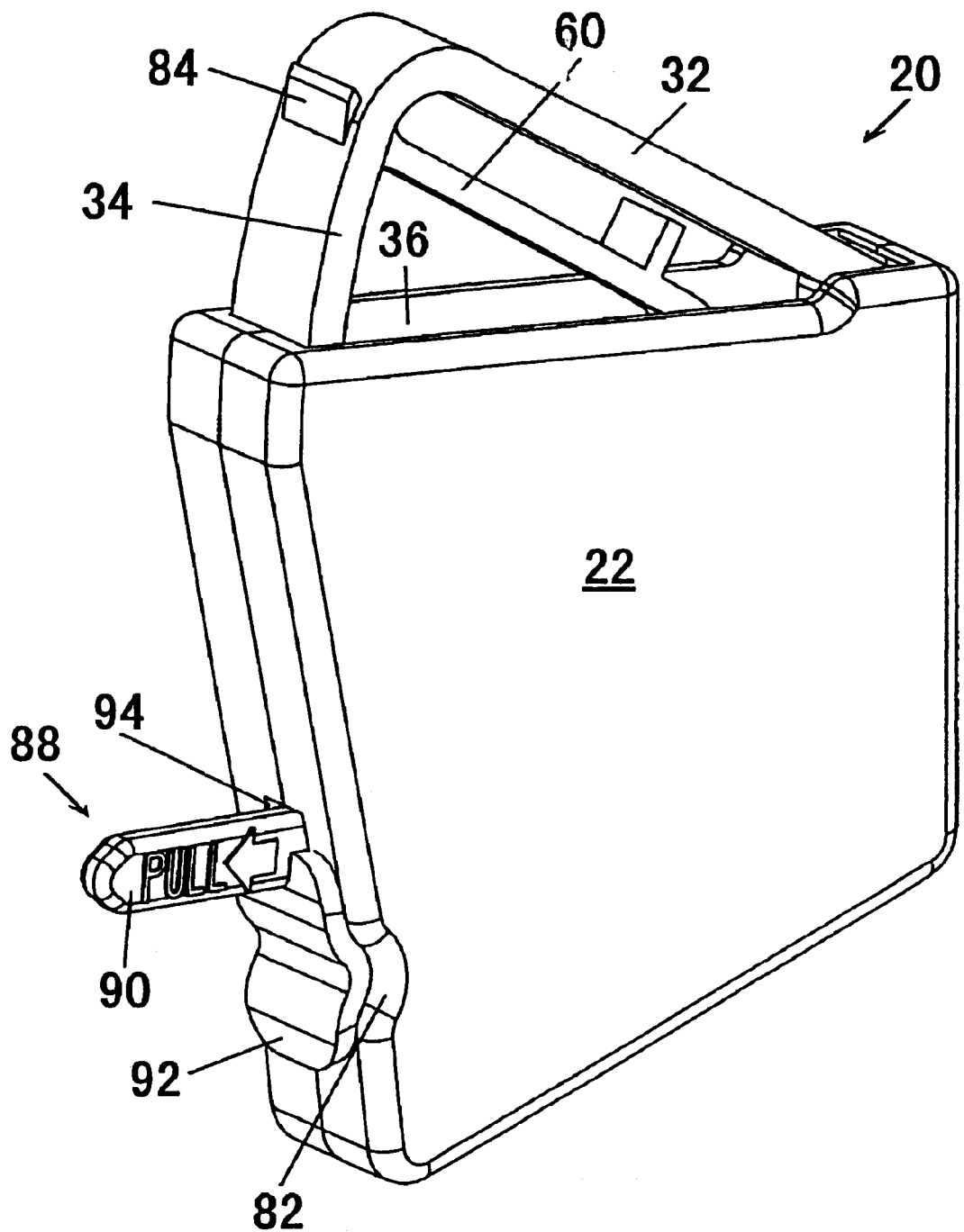
FIG. 1 is a perspective view of an illustrative skin incision lancet apparatus constructed in accordance with the teachings of the present invention.
Figure 2:
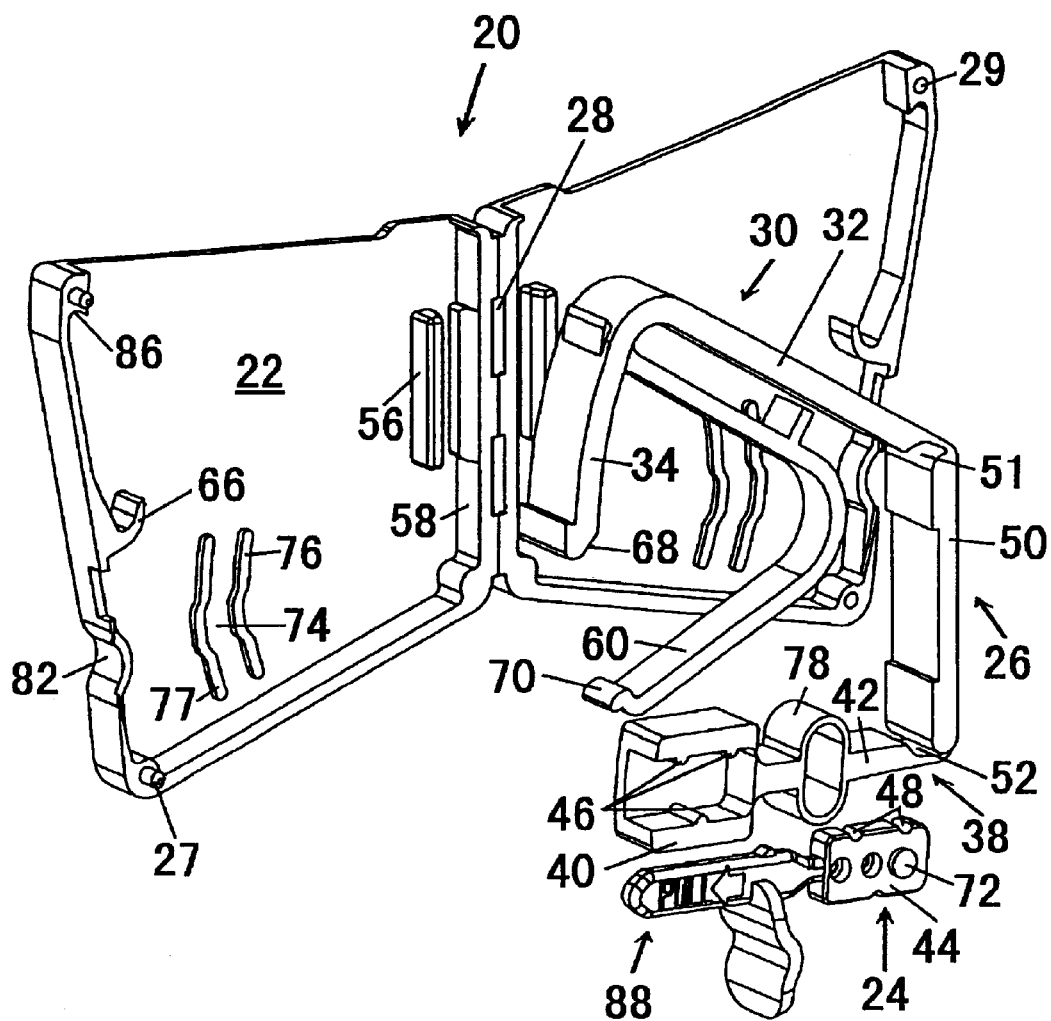
FIG. 2 is an exploded perspective view of the skin incision lancet apparatus of FIG. 1.

Referring now more particularly to FIGS. 1 and 2 there is shown an illustrative incision lancet device 20 which can be used to produce an incision of a precisely controlled length and depth in a bodily surface of a patient, for example a heel, in accordance with the present invention. The incision device of the present invention has a relatively simple and very stable construction which makes it very difficult to trigger the device inadvertently and also enables the device to have a relatively long shelf-life even at elevated temperatures. Moreover, the incision device provides very accurate performance and can be manufactured and assembled, as well as packaged and sterilized, in a simple and cost-efficient manner.

Figure 3:
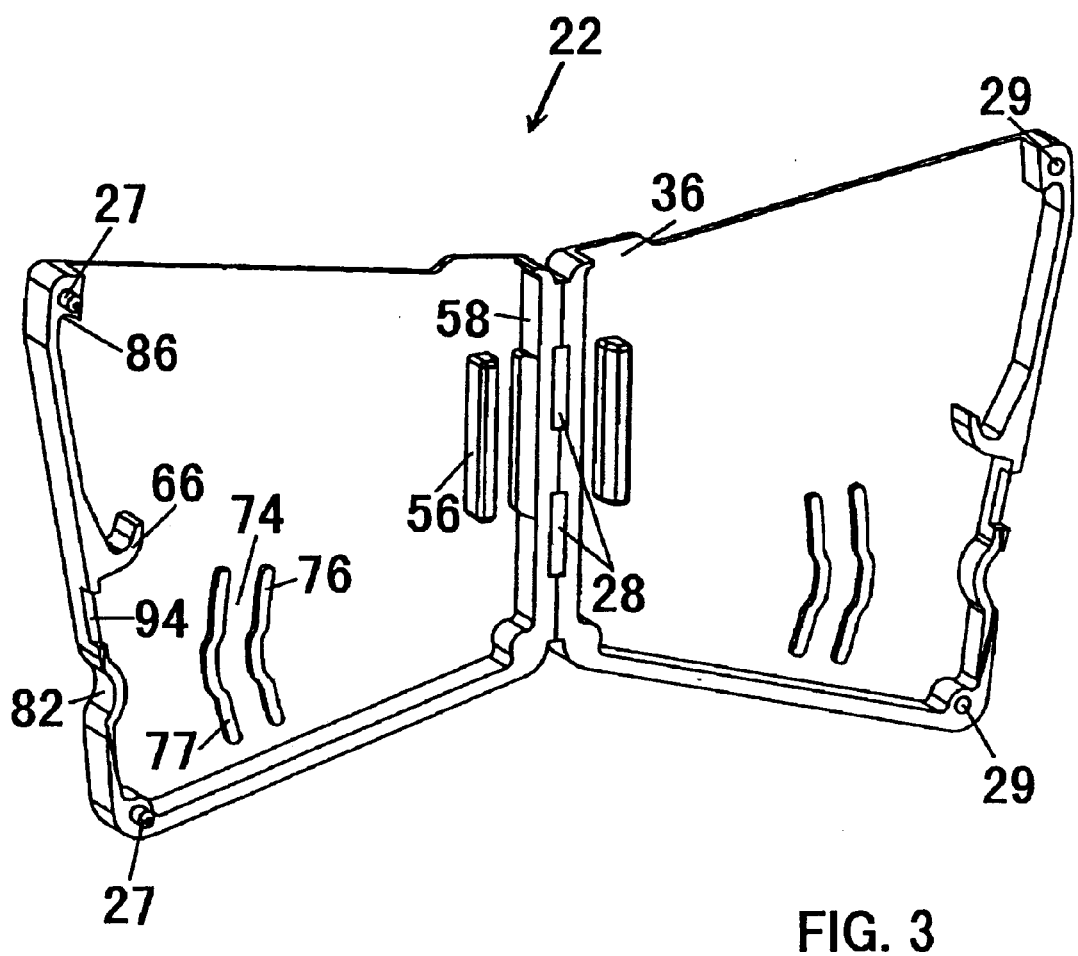
FIG. 3 is a perspective view of the housing of the incision apparatus.

The illustrated incision device 20 generally includes a housing 22, an incising element or lancet blade 24, which in this instance incorporates and inclined cutting edge (see, e.g. FIG. 7), and a firing means or system 26 which upon triggering moves the lancet blade through a cutting stroke that can create a precise incision in the skin of a patient. As shown in FIG. 3, the housing 22, in this instance, comprises two identical mating halves which can be formed of a plastic resin material. In the illustrated embodiment, the two halves of the housing 22 are connected together at one side thereof by a hinge 28 and have a mating post 27 and recess 29 arrangement at the corners of the opposing side such that the two halves of the housing can be snapped together.

Figure 8:
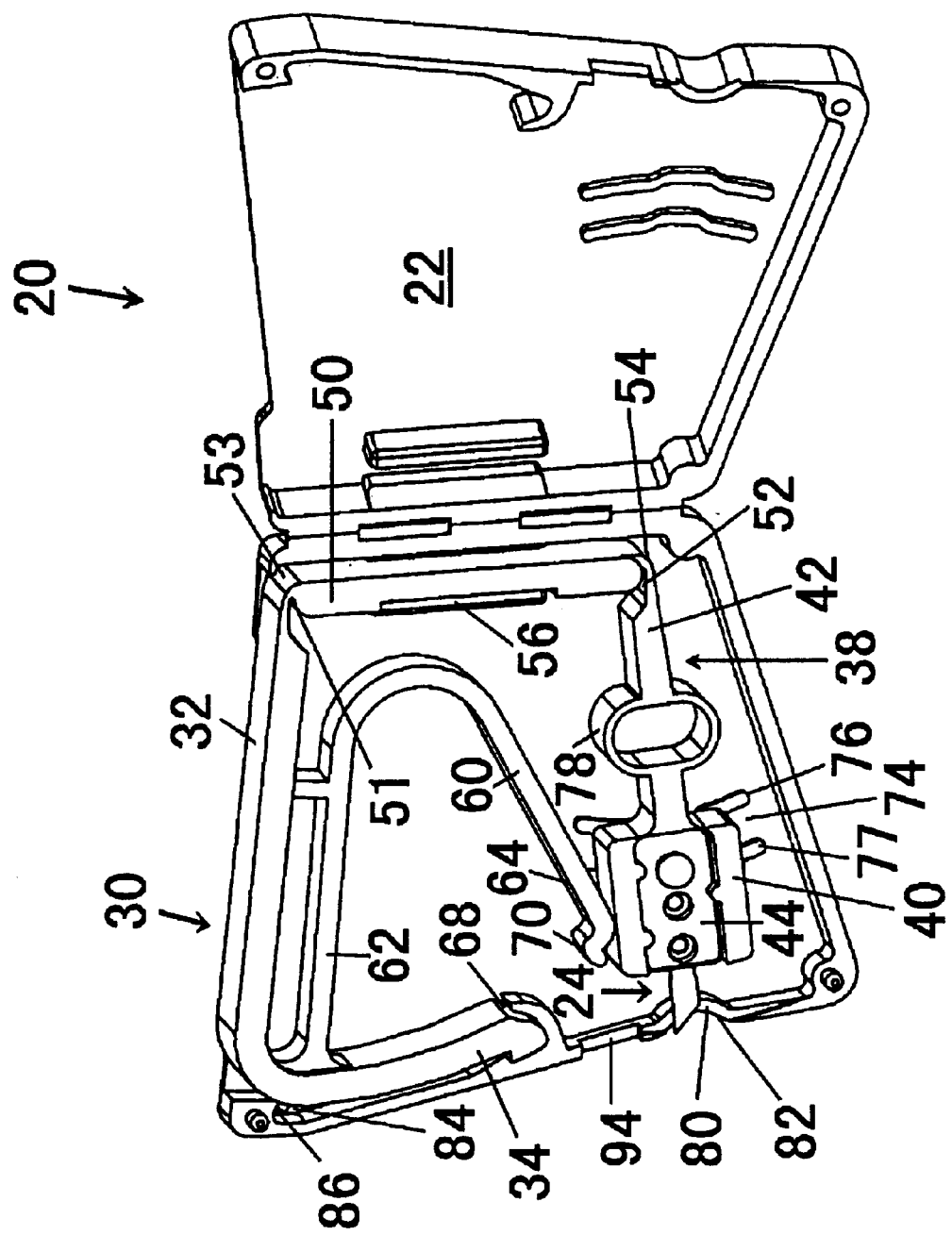
FIG. 8 is a partially cut-away perspective view of the incision apparatus showing the trigger arm fully depressed into the firing position and the spring element discharging so as to drive the lancet blade through its cutting stroke.

For actuating or firing the incision device 20, the firing system 26 includes a trigger means or mechanism 30 movable between a ready-to-fire position (e.g., shown in FIGS. 1 and 6) and a firing position (e.g., shown in FIG. 8). The trigger mechanism 30, in this case, includes a trigger arm 32 having a trigger actuating element 34. As shown in FIG. 1, the trigger arm 32 extends angularly through an opening 36 in the top of the housing 22 and away from the housing so as to be easily accessible for actuation by a user. The trigger actuating element 34 is connected to the trigger arm 32 adjacent the free end thereof (the left with reference to FIG. 1) and extends away from the trigger arm and back towards and into the housing through the opening 36. As is described in greater detail below, the trigger mechanism 30 can be used to actuate the incision device through depressing the trigger arm 32 such that it is displaced downwardly towards the housing.

For supporting and guiding the lancet blade 24 as it moves through its cutting stroke, the firing system 26 also includes a lancet guide means or assembly 38. In the illustrated embodiment, the lancet guide assembly 38 includes a lancet blade holder 40 which is connected to a lever or guide arm 42 that is movable between an unfired (see, e.g., FIGS. 6 and 7) and a fired position (see, e.g., FIG. 11). The blade holder 40 is configured to receive in a recess formed therein a base portion 44 of the lancet blade 24 as best shown in FIG. 2. In particular, the blade holder 40 includes in this case three ridges 46 which are configured to engage three complementary notches 48 on the base portion 44 of the lancet blade and secure the lancet blade 24 in the holder when the blade is mounted in the proper orientation.

Figure 4:
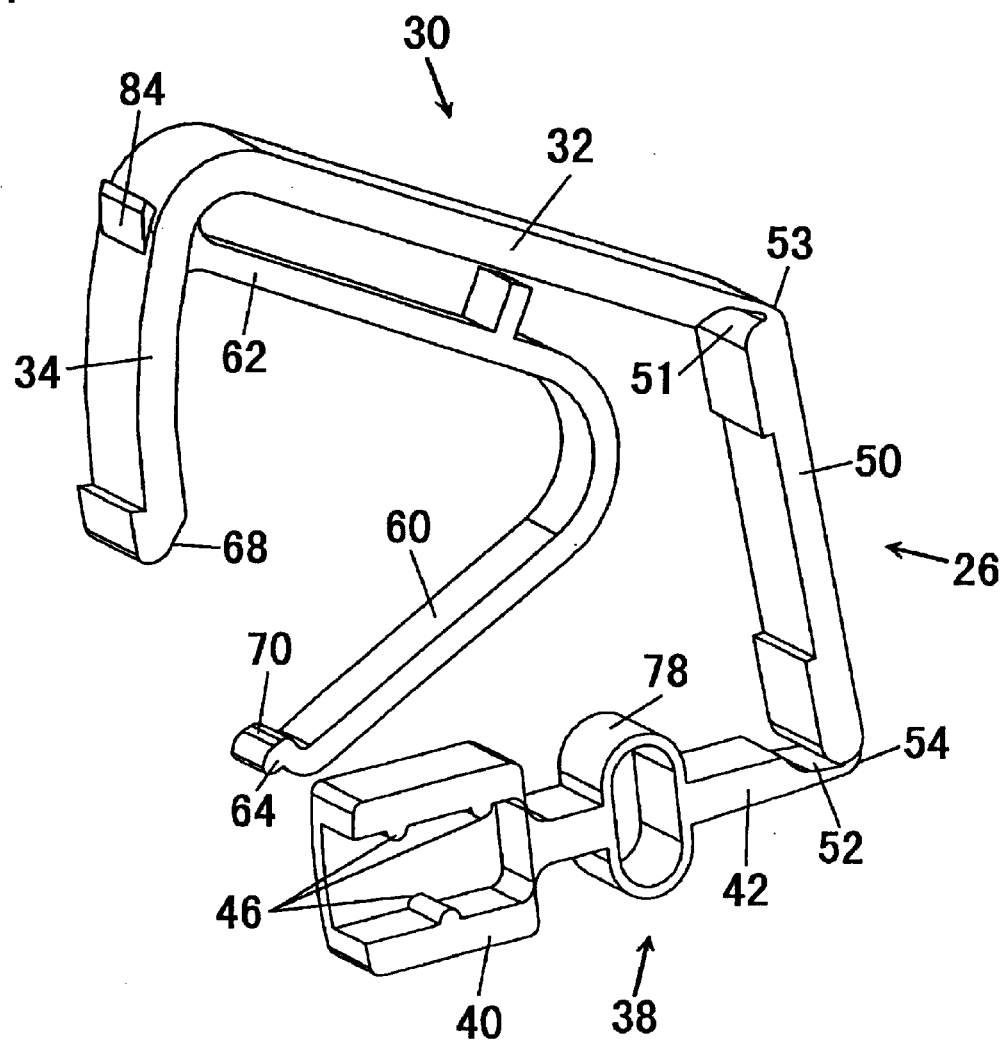
FIG. 4 is a front perspective view of the firing system of the incision apparatus.
Figure 6:
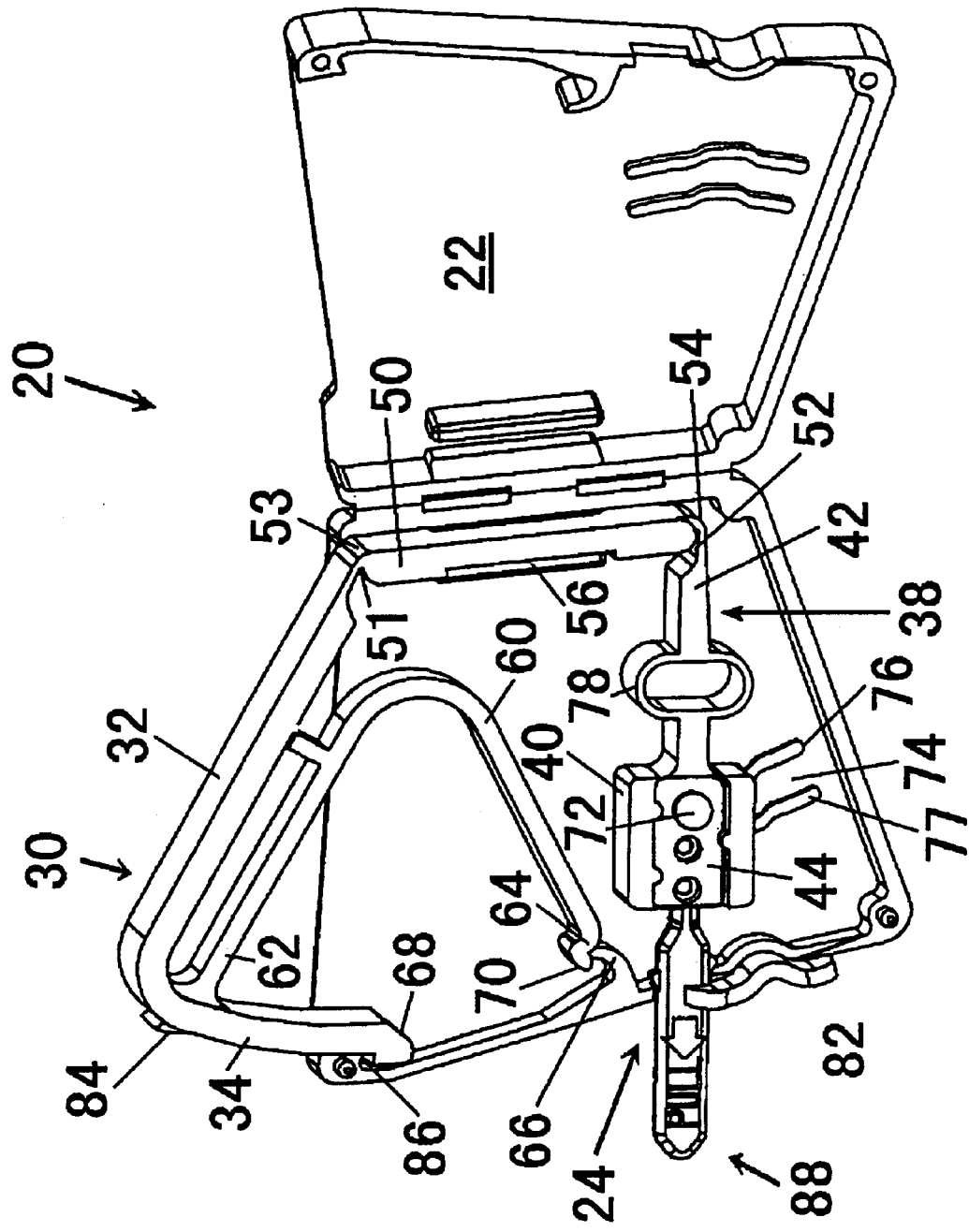
FIG. 6 is a partially cut-away perspective view of the incision apparatus in a ready-to-fire condition prior to use.

For ease of manufacture and assembly of the incision device 20, the trigger mechanism 30 and lancet guide assembly 38 of the firing system 26 can be integrated into a one piece construction through an intermediate connecting arm 50. As shown in FIGS. 2, 4 and 6, the intermediate connecting arm 50 is connected to and extends between the respective ends (the right ends in FIGS. 2, 4, and 6) of the trigger arm 32 and lancet guide arm 42. To enable hinge-like pivotal movement of the trigger arm 32 and the lancet guide arm 42, notches 51, 52 are formed at the respective junctures between the trigger arm and the connecting arm and the lancet guide arm and the connecting arm. In particular, the notch 51 between the trigger arm 32 and the intermediate connecting arm 50 defines a first fulcrum or pivot point 53 about which the trigger arm can be rotated. Likewise, the notch 52 between the lancet guide arm 42 and the intermediate connecting arm 50 defines a second fulcrum or pivot point 54 about which the lancet guide arm can pivot. To fix these pivot points in stationary positions relative to the housing 22, the intermediate connecting arm 50 is mounted to the housing between an internal ledge 56 and a side 58 of the housing 22 as shown in FIG. 6.

For driving the lancet guide assembly 38, and in turn, the lancet blade 24, through the cutting stroke, the firing system 26 includes a spring means or element 60. In accordance with one aspect of the present invention, to provide the incision device 20 with a more stable construction, the spring element 60 can be configured such that it can be assembled into the device in an unbiased condition and remain in that unbiased condition until the device is actuated or fired. Accordingly, the incision device 20 is easier to assemble as well as much less prone to inadvertent discharge. Moreover, since the spring element 60 is not biased it does not apply any force which would stress other elements of the incision device such as the lancet guide assembly 38, thus, malfunctions are much less likely even when the device has been stored for a relatively long period of time or at elevated temperature. Additionally, since in the illustrated embodiment the spring element 60 is integrated directly into the trigger mechanism 30, the entire firing system 26, including the trigger mechanism, the lancet guide assembly 38 and the spring element 60, can be molded in a single piece, thereby substantially reducing manufacturing and assembly costs.

Figure 7:
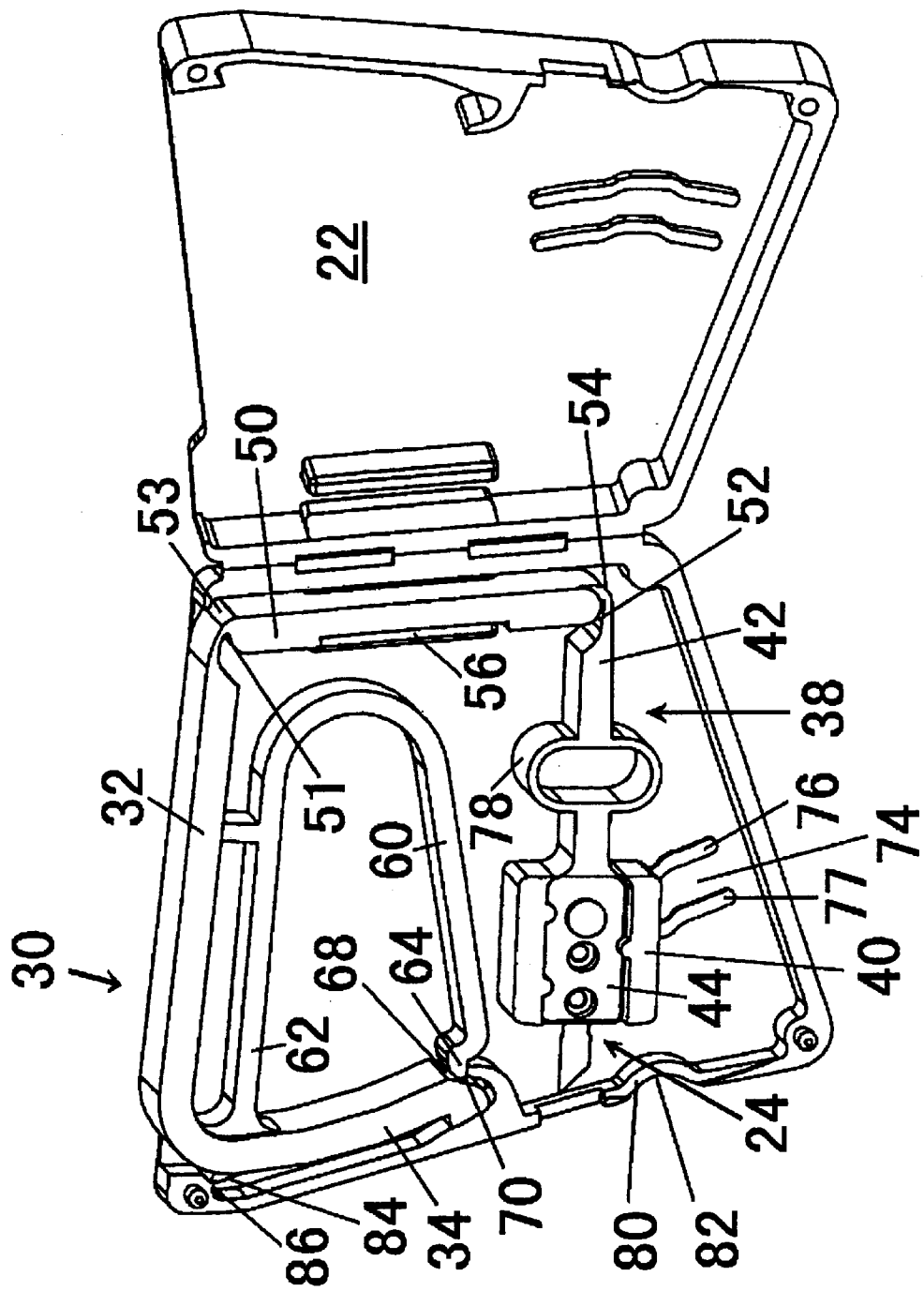
FIG. 7 is a partially cut-away perspective view of the incision apparatus showing the trigger arm almost fully depressed into the firing position and the spring element in full compression prior to driving the incising element.

As shown in FIGS. 6 and 7, the spring element 60 is interrelated with the trigger mechanism 30 such that the movement of the trigger arm 32 from the ready-to-fire towards the firing position biases the spring element. In the illustrated embodiment, the spring element 60 has a generally V-shaped configuration and is constructed of a material which enables the spring element to be resiliently compressible. Preferably, the spring element 60 is constructed of a plastic resin material in order to reduce costs, however, it will be appreciated other materials could be used, including metal. As shown in FIG. 6, a first end 62 of the spring element is connected to the trigger actuating element 34 while a free end 64 of the spring element is arranged, when the incision device 20 is assembled, in engagement with an internal catch 66 formed on the inside of one side of the housing 22. Thus, when the trigger arm 32 is pivoted towards the firing position, the movement of the trigger actuating element 34 causes the first end 62 of the spring element to move towards the free end 64 of the spring element which is held in place by the catch 66 thereby biasing the spring element.

For releasing the spring element 60 once it is biased, the trigger actuating element 34 is configured so as to disengage the spring element from the catch once the trigger arm 32 reaches the firing position. More specifically, an inclined cam surface 68 is provided on an end of the trigger actuating element 34 which engages a cooperating cam surface 70 at the end of the spring element 60 to push the free end 64 of the spring element 60 off of the internal catch 66 as shown in FIGS. 7 and 8.

Figure 10:
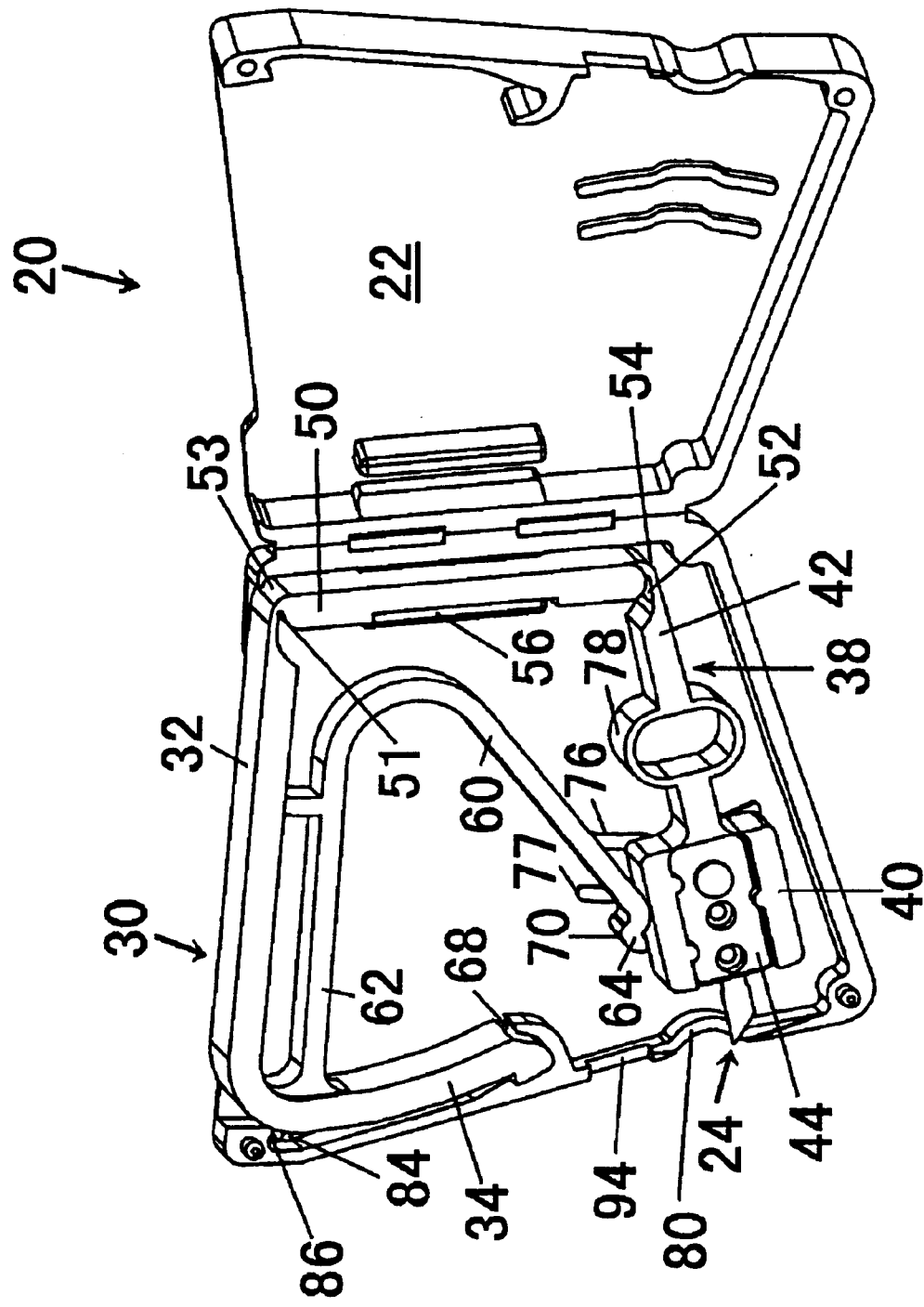
FIG. 10 is a partially cut-away perspective view of the incision apparatus showing the lancet blade near the end of its cutting stroke.
Figure 11:
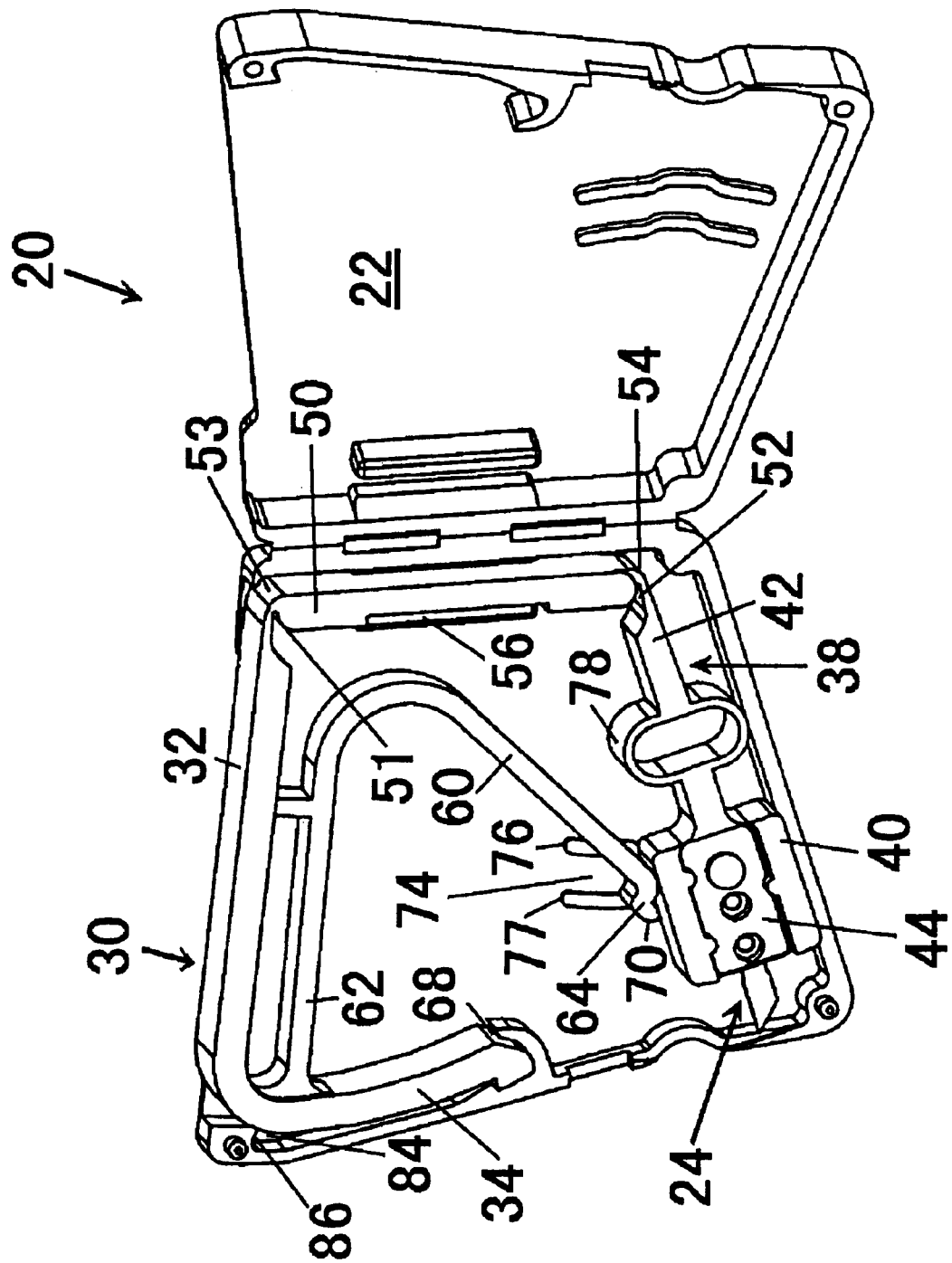
FIG. 11 is a partially cut-away perspective view of the incision apparatus showing the firing system after completion of a firing sequence.

In order to drive the lancet blade 24 through the cutting stroke, the spring element 60 is arranged such that when it is released, the free end 64 of the spring element strikes or hammers and then pushes the lancet blade holder 40 of the lancet guide assembly 38. As shown in FIG. 8, the initial hammering force causes the lancet guide arm 42 to begin to pivot about the pivot point 54 defined by the notch 52 between the lancet guide arm and the connecting arm 50 thereby starting movement of the blade holder 40 and, in turn, the lancet blade 24 through an arcuate path. After the initial hammering force is applied, the free end 64 of the spring element 60 comes over the external surface of the blade holder 40 (as shown in FIGS. 8, 10 and 11) and continues to push the blade holder 40 through the arcuate path resulting from the pivotal movement of the guide arm 42 from the unfired to the fired position.

Figure 4A:
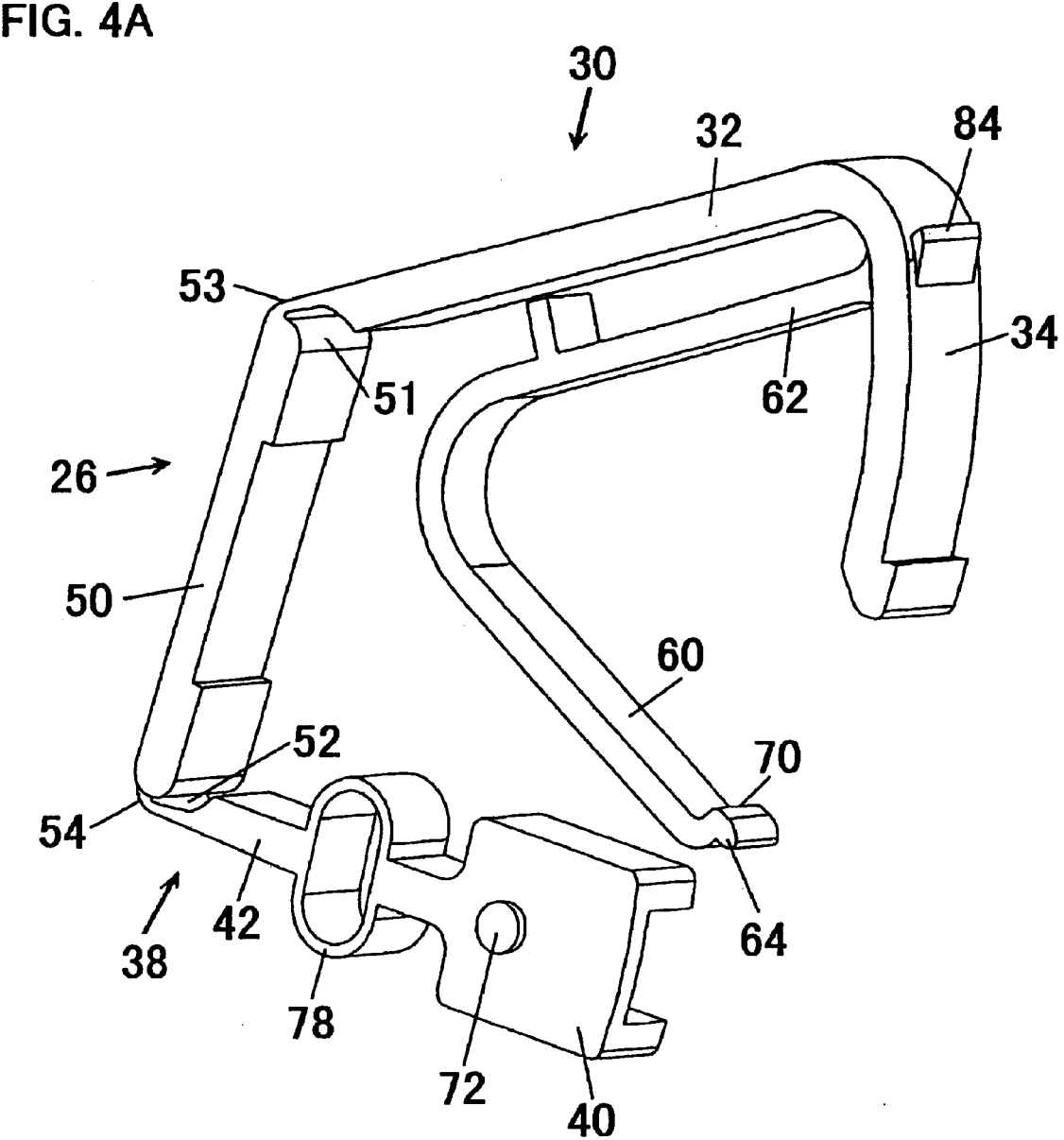
FIG. 4A is a rear perspective view of the firing system of the incision apparatus.
Figure 9:
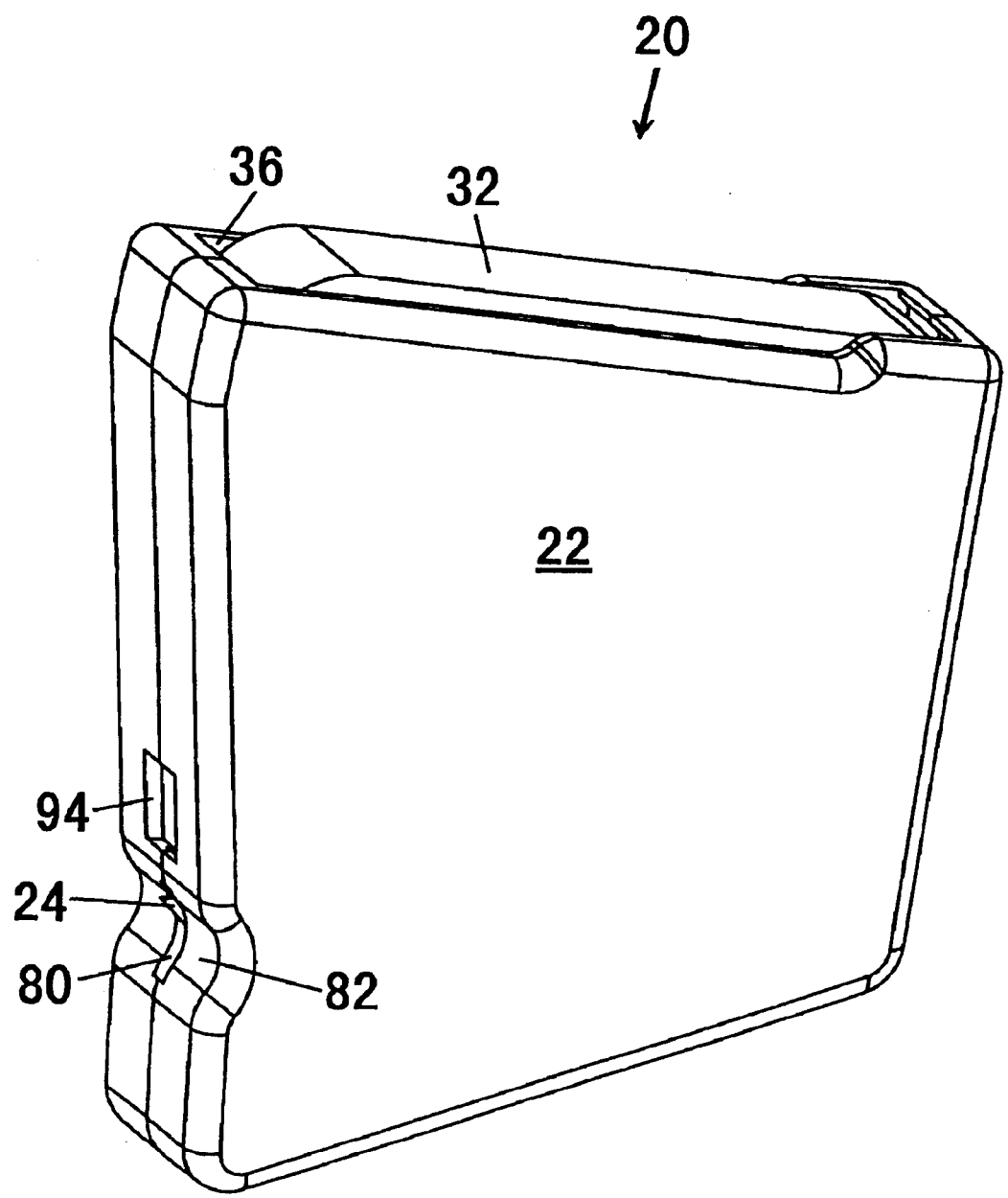
FIG. 9 is a perspective view of the assembled incision apparatus showing the lancet blade moving through its cutting stroke.

To ensure that the cutting stroke of the lancet blade 24 is precisely controlled, the lancet guide assembly 38 is adapted such that the blade holder 40 moves through a precise arcuate path as the lancet guide arm 42 is pivoted between the unfired and fired positions. Specifically, the blade holder 40 and the base portion 44 of the lancet blade include projecting lugs 72 (FIGS. 4 and 4A) which are received in a cooperating groove 74 defined by a pair of ridges 76, 77 formed in the housing 22 (see, e.g. FIG. 6). Moreover, the guide arm 42 includes, in this instance, a generally oval-shaped expandable section 78 which permits linear expansion of the lancet guide arm, as exemplified by the change in shape of the expandable section 78 in FIGS. 7 and 8. As will be appreciated, the expandable section 78 of the lancet guide arm 42 permits the lancet holder 40 to be guided via the groove 74 in the housing through a precise arcuate path in which the lancet blade 24 is first brought into a cutting position (FIGS. 7–8), then executes a cutting stroke (FIGS. 8–10) and finally moves into a safe at-rest position (FIG. 11).

The expandable section 78 preferably has a shape, such as the oval-shape in the illustrated embodiment, which has bilateral symmetry. The bilaterally symmetrical shape of the expandable section 78 allows the lancet guide arm 42 to expand only in a linear direction even though the spring element applies a force in a generally lateral direction, thereby ensuring that precise control over the profile of the arcuate cutting path is maintained. More specifically, the bilaterally symmetrical shape of the expandable section 78 helps prevent the guide arm 42 from being angularly deflected as a result of the initial hammering force applied by the spring element 60, the forces resulting from movement of the projecting lugs 72 through the groove 74, and the forces resulting from the lancet blade 24 cutting through the skin.

As shown in FIG. 7, before the incision device 20 is fired, the lancet blade 24 is arranged entirely inside of the housing 22. During the firing sequence, the lancet blade 24 first moves into a position wherein the blade extends through a slot 80 formed in an arcuately shaped skin engaging portion 82 of the side of the housing 22, as shown, for example, in FIG. 9. The lancet blade 24 then moves through a precise cutting stroke. After the cutting stroke is completed, the configuration of the guiding groove 74 in the housing causes the lancet blade 24 to retract back into the housing 22, as shown in FIG. 11, so that the incision device can be disposed of without any exposed cutting edges which may cause injury.

Of course, it will be understood that the incision device 20 can be designed to create an incision having a wide variety of different dimensions. For example, in one preferred embodiment, through varying the configuration of the housing 22, an incision device can be provided which is capable of producing an incision of anywhere between approximately 0.5 mm to 2.0 mm in depth.

In order to prevent the incision device 20 from being reused and thereby compromising the sterility of the device, the trigger mechanism 30 is configured such that the device can only be fired once. Specifically, once the trigger arm 32 reaches the firing position, a ridge 84 formed on the trigger actuating element 34 engages a cooperating edge 86 formed in the housing 22 to prevent return of the trigger arm 32 toward the ready-to-fire position as shown in FIG. 8. Thus, the engagement of the ridge 84 with the housing prevents the incision device 20 from being re-loaded once it has been fired.

Figure 5:
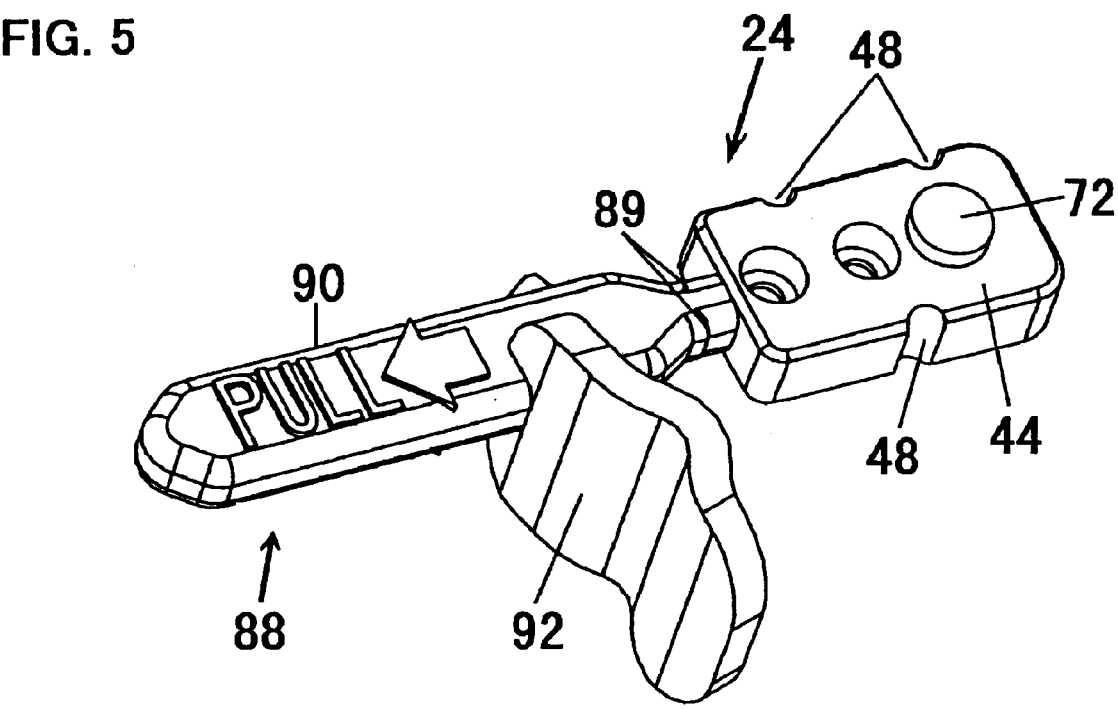
FIG. 5 is a perspective view of the incision element or lancet blade of incision apparatus.

To simplify sterilization and packaging of the incision device 20, a removable cover may be provided which covers both the lancet blade 24 and the skin-engaging portion 82 of the housing. More particularly, as shown in FIGS. 1, 5 and 6, the base portion 44 of the lancet blade 24 includes a snap-off removable cover 88 which may be disengaged from the base portion 44 via a pre-cut slit 89 to uncover the lancet blade 24. In the illustrated embodiment, the removable cover 88 includes a protective sheath portion 90 which shields the lancet blade 24 from contamination and a protective flange portion 92 which protects the arcuate skin engaging portion 82 of the housing 30 against contamination. As shown in FIGS. 1 and 6, the cover extends through an opening 94 in the side of the housing 22, such that it can be easily grasped and removed from the lancet blade 24, which is arranged entirely within the housing, prior to use of the incision device. Because of the removable cover 88, only the lancet blade 24 itself must be sterilized and thus, there is no need to encase the entire incision device in sterilized packaging.

To use the incision-type device 20, the cover 88 is pulled from the lancet blade 24 through the opening 94 in the housing so as to uncover the cutting edge thereof and to expose the skin engaging portion 82 of the housing. Next, the skin engaging portion 82 of the housing 22 is pressed against a patient's skin. Thereafter, the trigger arm 32 of the trigger mechanism 30 is simply pressed downwardly toward the firing position, as shown, for example, in FIG. 7, in order to fire the incision device 20. Once the trigger arm 32 reaches the firing position, the spring element 60 is displaced from the catch 66 in the housing and strikes the blade holder, pushing it through the arcuate cutting cycle and into the safety position again within the housing. As will be appreciated, having the trigger arm and the opening for the lancet blade oriented on adjoining, as opposed to opposing, sides of the housing also makes the device of the present invention much easier to use.

From the foregoing it can be seen that an incision device is provided which has a very stable construction which helps prevent inadvertent firing or discharge of the device as well as enables the device to perform reliably after having been stored for a prolonged period of time, even at high temperatures. Moreover, the device has a simple construction which enables it to be manufactured and assembled in a cost-effective manner.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and the scope of the invention as defined by the following claims.

What is claimed is:

1. An apparatus for producing a precisely controlled incision in a bodily surface comprising:

a housing;

a lancet blade carried by a lancet guide assembly which includes a lancet guide arm mounted within the housing for pivotal movement and a lancet guide which guides the lancet blade through an arcuate cutting stroke during which the lancet blade extends through an opening in the housing when the lancet guide arm is pivoted between an unfired and a fired position, a trigger mechanism including a trigger arm mounted in the housing for pivotal movement between a ready-to-fire position and firing position, a spring element arranged within the housing such that it is in an unbiased condition when the trigger arm is in the ready-to-fire position and is biased as the trigger arm pivots towards the firing position;

the trigger mechanism and spring element being configured such that the biased spring element is released from a catch when the trigger arm reaches the firing position; and the spring element being arranged such that when it is released it exerts a force on the lancet guide arm which pivots the guide arm from the un-fired to the fired position and thereby moves the lancet blade through the cutting stroke.

2. The incision apparatus according to claim 1 further including a connecting portion mounted in the housing which joins the trigger mechanism and the lancet guide assembly.

3. The incision apparatus according to claim 2 wherein the connecting portion defines respective pivot points for the lancet guide arm and the trigger arm.

4. The incision apparatus according to claim 3 wherein the respective pivot points for the lancet guide arm and the trigger arm are defined by respective notches at a juncture between the connecting portion and the trigger arm and a juncture between the connecting portion and the lancet guide arm.

5. The incision apparatus according to claim 2 wherein the connecting portion, trigger mechanism and lancet guide assembly are integrally formed.

6. The incision apparatus according to claim 1 wherein the spring element is connected to the trigger arm.

7. The incision apparatus according to claim 6 wherein the spring element has a resiliently compressible generally V-shaped configuration having a first end connected to a trigger actuating element of the trigger arm and a free end which is engaged with the catch when the trigger arm is in the ready-to-fire position such that movement of the trigger arm from the ready-to-fire to the firing position compresses the spring element.

8. The incision apparatus according to claim 7 wherein the free end of the spring element strikes and then cams over the a surface of the lancet guide arm when the biased spring element is released.

9. The incision apparatus according to claim 1 wherein the trigger arm is configured such that when the trigger arm reaches the firing position the trigger arm engages the spring element and releases the spring element from the catch.

10. The incision apparatus according to claim 8 wherein the trigger arm includes a camming surface which engages a complementary camming surface on the spring element so as to release the spring element from the catch when the trigger arm reaches the firing position.

11. The incision apparatus according to claim 1 wherein the lancet guide comprises a guide groove arranged on the housing which engages a complementary lug carried by the lancet guide arm.

12. The incision apparatus according to claim 1 wherein the lancet guide assembly is configured such that the lancet blade is arranged entirely within the housing when the guide arm is in the un-fired position and when it is in the fired position.

13. The incision apparatus according to claim 1 wherein the lancet blade is carried on the lancet guide assembly by a blade holder included on the lancet guide arm.

14. The incision apparatus according to claim 1 wherein the trigger arm is configured such that it cannot return to the ready-to-fire position after it has been pivoted to the firing position.

15. The incision apparatus according to claim 14 wherein the trigger arm includes a ridge which engages a complementary edge carried on the housing when the trigger reaches the firing position so as to prevent the trigger arm from returning to the ready-to-fire position.

16. The incision apparatus according to claim 1 wherein a snap-off removable protective cover is provided on the lancet blade for protecting the lancet blade from contamination.

17. The incision apparatus according to claim 16 wherein the protective cover includes a flange portion which covers a skin-engaging portion of the housing to protect it against contamination.

18. The incision apparatus according to claim 1 wherein the lancet guide arm includes an expandable section which permits linear expansion of the guide arm as the guide arm is pivoted between the unfired and fired positions.

19. The incision apparatus according to claim 18 wherein the expandable section has a bilaterally symmetrical shape.

20. The incision apparatus according to claim 19 wherein the expandable section has an oval-shape.

* * * * *